United States Patent
Mann et al.

(10) Patent No.: US 7,402,251 B2
(45) Date of Patent: Jul. 22, 2008

(54) CHROMATOGRAPHY COLUMN AND METHOD OF OPERATION

(75) Inventors: William H. Mann, Chattanooga, TN (US); Mickey Mann, Chattanooga, TN (US)

(73) Assignee: Mann Welding Company, Chattanooga, TN (US)

( * ) Notice: Subject to any disclaimer, the term of this patent is extended or adjusted under 35 U.S.C. 154(b) by 241 days.

(21) Appl. No.: 11/320,078

(22) Filed: Dec. 28, 2005

(65) Prior Publication Data

US 2007/0144955 A1    Jun. 28, 2007

(51) Int. Cl.
    *B01D 15/08* (2006.01)
(52) U.S. Cl. .................... 210/656; 210/198.2
(58) Field of Classification Search ............. 210/198.2, 210/635, 656, 659, 143; 95/82; 96/101
    See application file for complete search history.

(56) References Cited

U.S. PATENT DOCUMENTS

| | | | | |
|---|---|---|---|---|
| 4,978,290 A | * | 12/1990 | Fukuhara | 425/147 |
| 5,158,675 A | * | 10/1992 | Allington et al. | 210/198.2 |
| 5,360,320 A | * | 11/1994 | Jameson et al. | 417/4 |
| 5,681,474 A | * | 10/1997 | Gunther et al. | 210/656 |
| 6,458,273 B1 | * | 10/2002 | Krakover et al. | 210/198.2 |
| 6,736,974 B1 | * | 5/2004 | Mann | 210/656 |
| 2002/0195391 A1 | * | 12/2002 | Young et al. | 210/656 |
| 2003/0170127 A1 | * | 9/2003 | Muenzenmaier et al. | 417/342 |
| 2004/0016701 A1 | * | 1/2004 | Hauck et al. | 210/656 |
| 2004/0099604 A1 | * | 5/2004 | Hauck et al. | 210/656 |
| 2004/0188333 A1 | * | 9/2004 | Allington et al. | 210/198.2 |
| 2006/0196832 A1 | * | 9/2006 | Perreault et al. | 210/656 |
| 2006/0219616 A1 | * | 10/2006 | Noyes et al. | 210/198.2 |
| 2007/0012626 A1 | * | 1/2007 | Andersson et al. | 210/656 |
| 2007/0090053 A1 | * | 4/2007 | Windahl | 210/656 |

* cited by examiner

*Primary Examiner*—Ernest G Therkorn
(74) *Attorney, Agent, or Firm*—Stephen J. Stark; Miller & Martin PLLC

(57) ABSTRACT

A chromatography column is normally filled with a slurry of media for operation. A piston normally compacts the slurry in the column. The piston moves through a cavity in communication with both a slurry inlet and slurry ports which are in communication with the interior of the chromatography column. A controller receiving inputs from at least one of position sensors and a pressure sensor directs movement of the plunger in an operational step selected from the group of a selected movement and up to a selected pressure.

20 Claims, 2 Drawing Sheets

CHROMATOGRAPHY COLUMN AND METHOD OF OPERATION

BACKGROUND OF THE INVENTION

1. Field of the Invention

The present invention relates an apparatus and method of operating a chromatography column and, more particularly, to such a chromatography column and a method for effectively packing media and/or ensuring that the top flow adapter remains within a tolerance of being level and/or automatically moving the top flow adapter to at least one predetermined position.

2. Description of Related Art

Chromatography is a process of separating the components of a mixture of chemical substances through the percolation of fluid through a body or bed of comminuted or porous rigid material, known as media. In the process, the various component are often resolved, or separated, by their selective retardation as they are transported through the bed by a moving fluid or buffer. A solution of the substances to be separated becomes the moving phase of the system passing through the interstices in the stationary or continuous phase which are finely divided particles, possibly in the form of a gel slurry.

The substances in the moving phase are poured into the top of a chromatography column filled with the finely divided material, i.e., the media, that can absorb differentially the substances to be separated. The particular material used for the media varies widely with the substances to be separated. As the solution percolates down the column the components are separated from the buffer fluid which may be pumped back into the top of the column so as to again pass down through the bed as a carrier. The different substances as they travel down the column at different rates form bands of the different substances which are individually collected at the outlet.

A chromatography column typically comprises a hollow vertically disposed cylindrical housing including a liquid dispensing section, also referred to as a top flow adapter or plunger in many embodiments, at the upper end and through which the buffer and substances to be separated are dispensed to the media bed, and a liquid collecting section at the lower end for collecting the substances and buffer individually. The media or bed through which the buffer fluid and mixture to be separated and purified percolates is located between these sections. The liquid dispensing section and liquid collecting section may each include a respective distribution plate and at least one of the plates may be connected in an assembly with an axially movable plunger-like body positioned within the housing. After the column is charged with the bed media, the plunger body is often forced toward the bottom to compress or pressurize the media bed which has been poured into the column.

Prior art designs have allowed for the plunger to be moved with hydraulics manually controlled by an operator such as those shown and described in Applicant's U.S. Pat. No. 6,736,974, incorporated herein by reference. When the operator manually actuated the hydraulic controls of the prior art design, he or she would cause valves to open and shut to move the plunger up or down. There was no ability in this prior art design to have a controller move the plunger to a preset location. The operator had to attempt to stop at a preset location, which could be tricky. This is especially important during calibration steps. Also, there was no way to direct movement of one of the hydraulic cylinders independent of moving the other two in this prior art design.

The hydraulics in the prior art design provided a single hydraulic pressure from a control valve to each of three cylinders which moved the plunger. There was no way to ensure that each of the three cylinders moved in a manner to ensure that the top flow adapter moved in a level manner. If one side of the plunger became temporarily lodged on the inside of the column, or on pack material, it was easy for the plunger to become somewhat canted within the column. This is undesirable. The calculations performed by the pharmaceutical companies are often done with the assumption that the media pack is uniform. A lack of uniformity could adversely affect a run of product thereby causing unintended problems and a poor quality batch of pharmaceutical product.

The prior art packing technique involved an operator lowering a plunger until it stopped. If one of the cylinders encountered resistance, the other two could keep driving the plunger in a "canted" manner until they also stopped. A run of product could be performed with an unsatisfactory pack. This is believed to be undesirable.

Accordingly, a need exists to improve the operational methods by providing an improved chromatography column.

SUMMARY OF THE INVENTION

The present invention recognizes and addresses these needs and others.

Consequently, it is an object of at least one embodiment of the present invention to provide a chromatography column capable of maintaining the top flow adapter at least within a predetermined tolerance of being level.

It is another object of at least one embodiment of the present invention to provide a chromatography column capable of evenly packing media.

It is another object of at least one embodiment of the present invention to provide a chromatography column with a controller which can move the top flow adapter to at least one predetermined position.

Accordingly, the present invention provides a chromatography column having a cylinder defining a cavity for containing media therein. A top flow adapter or plunger is operatively coupled to a hydraulic piston moveable through at least a portion of the cavity within the cylinder during operation. A base is normally connected to the cylinder. The plunger may be operatively coupled to the hydraulic piston to adjust the height of the plunger above the base to provide a desired resin height between the plunger and the base for operation. The plunger may also be utilized to exert a force on the resin to "pack" the resin in the column.

A controller is also provided which preferably at least assists in providing one of a number of operational capabilities not provided in the prior art. The controller receives an input relative to at least two of three of the hydraulic cylinders utilized in the preferred embodiment relating to at least one of position and/or pressure. These inputs can be utilized to move the top flow adapter relative to the column to at least one predetermined position, to pack the column to a particular pressure at each of at least some of the pistons, and/or to maintain the top flow adapter within a range of being level separate valves are used for each hydraulic cylinder in such an embodiment.

The hydraulic system preferably includes at least one piston which is driven by at least one hydraulic cylinder. In the preferred embodiment, a plurality of hydraulic cylinders are utilized which are driven from a common hydraulic pressure source which is coupled to a controller. Unlike known prior art designs, the controller receives feedback related to each of the cylinders for increased performance capabilities. Upon receipt of a signal from a controller, the hydraulic cylinder(s) drive the hydraulic piston(s). Depending upon the configuration of the column, the piston(s) drive the plunger and/or the cylinder upwardly or downwardly.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENTS

Figure 1:
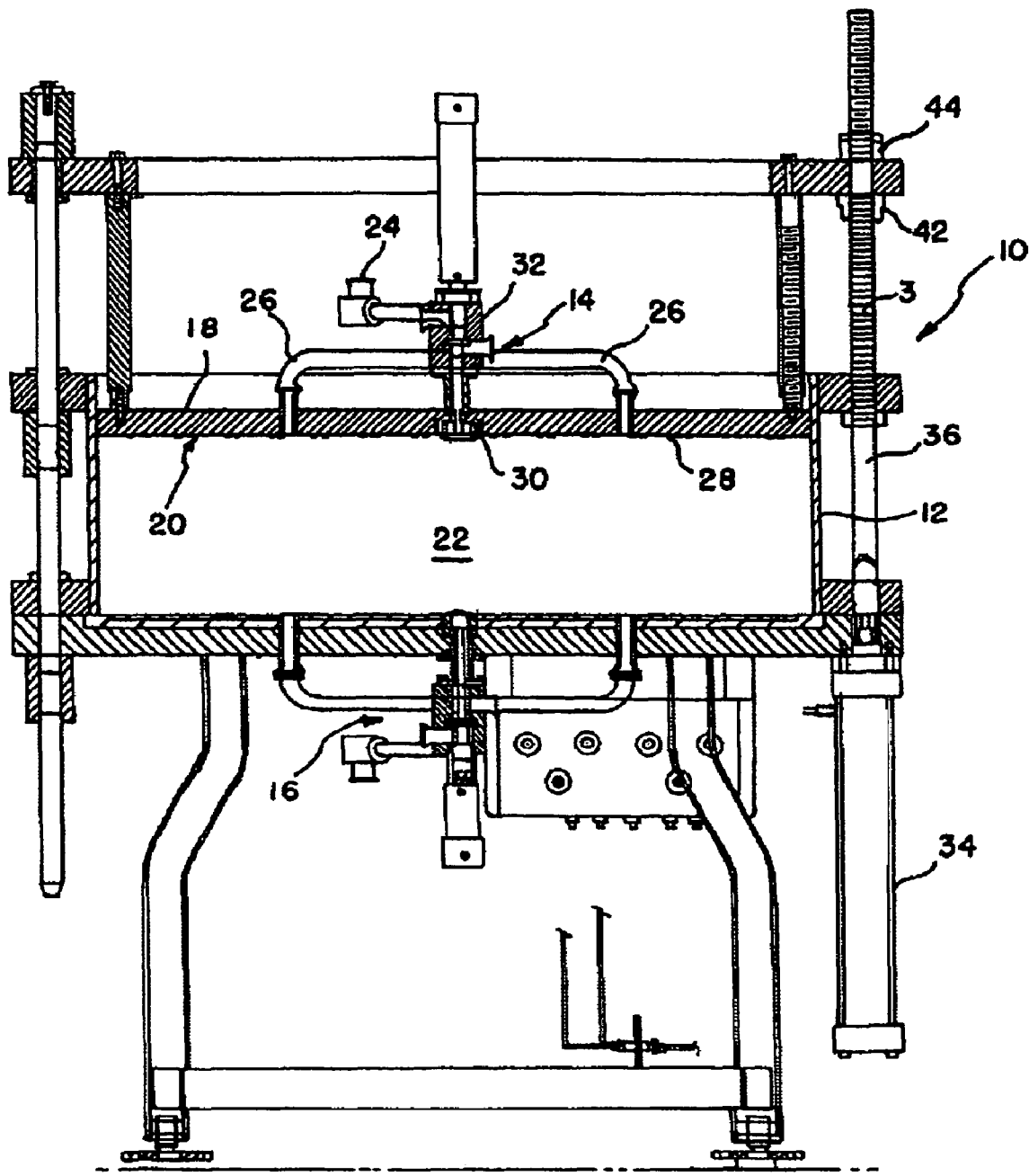
FIG. 1 is a side plan view of a chromatography column according to the present invention in a first operational position.
Figure 2:
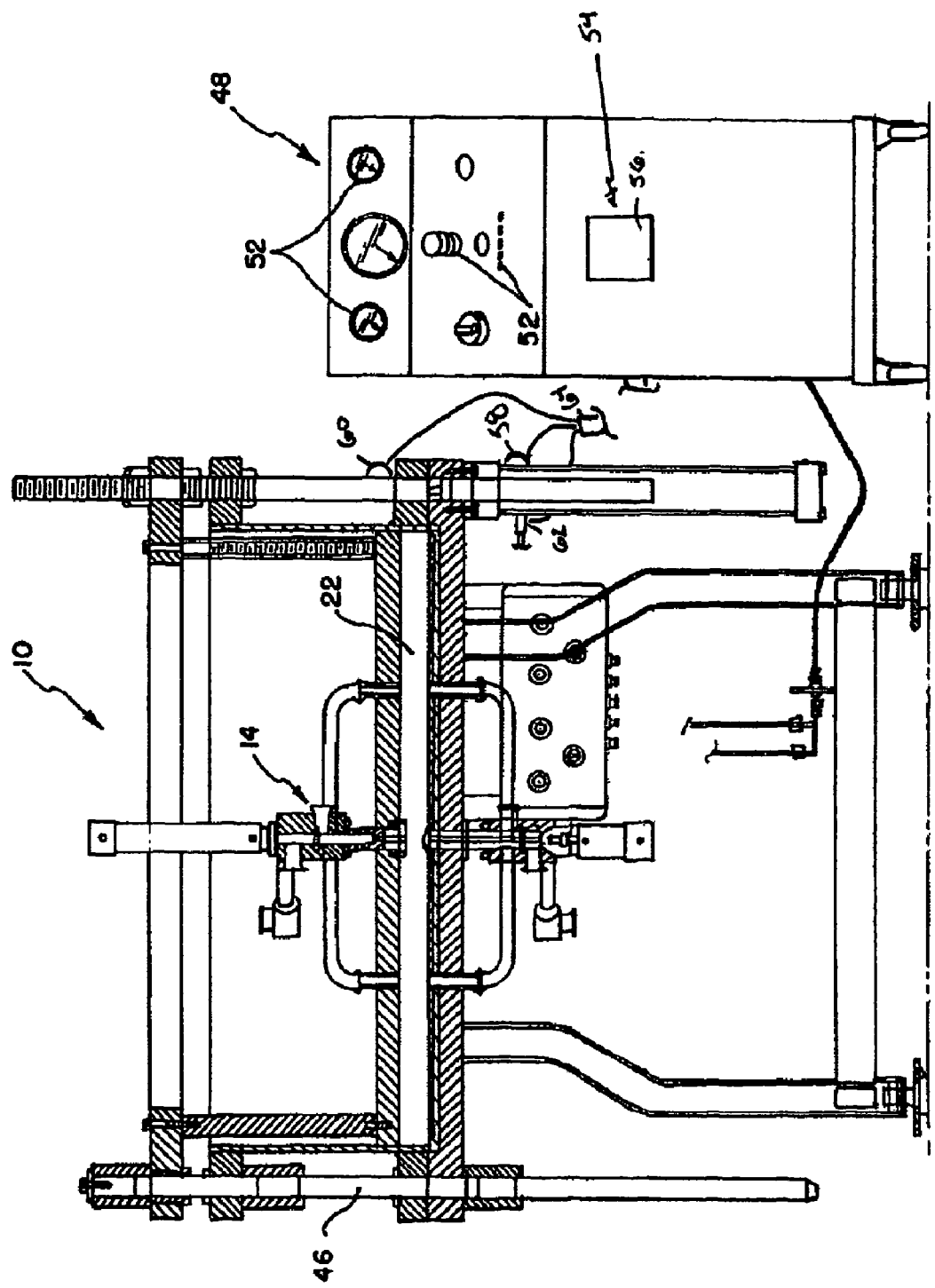
FIG. 2 is a side plan view of the chromatography column illustrated in FIG. 1 in a second operational position.

The present invention is concerned with a method and apparatus for permitting maintenance within a chromatography column which houses a slurry and/or media during operation. FIGS. 1-2 depict one such chromatography column 10 with the slurry removed. The column 10 comprises an elongated hollow cylindrical housing 12, or cylinder, having a dispersion section 14 at the top and a collecting section 16 at the bottom. The dispersion section 14 includes a cylindrical drum 18 having an upper cylindrical plunger head 20 formed at the lower end. The plunger 20 or top flow adapter is normally disposed within the upper portion of the housing 12 such as illustrated in the first operational position of FIG. 1. The plunger 20 may also be moved, such as with a drive system similar to the hydraulic arrangement illustrated to the second operational position of FIG. 2. The movement of the head 20 allows for the compression of media to "pack" resin and/or for the use of a particularly sized media column with the cavity 22 formed between the dispersion and collection sections 14,16 and/or between the plunger 20 and the base 64.

The dispersion section 14 may also include a product inlet 24 along with an inlet manifold 26 to distribute incoming fluid throughout a top portion of a resin column contained within the cavity 22. An inlet screen 28 may be connected to the plunger head 20 by connectors such as TEFLON™ snaps (not illustrated) and/or an inner clamp nut 30. The distributor plate 31 may be removable as well. A discussion of a distributor plate 31 design may be found in U.S. Pat. No. 6,190,560. A slurry fill valve 32 such as the valve taught in co-owned U.S. Pat. No. 6,190,560 may also be connected to the plunger head 20 and/or dispersion section 14. The slurry fill valve 32 provides a way to fill the cavity 22 with resin without the need to lift the plunger 28 out of the cavity 22 within the cylinder 12. Although a preferred dispersion section 14 is described, other dispersion sections designs could be utilized as well.

In order to move the plunger head 20 in an operational mode from the first operational position shown in FIG. 1 to the second operational position of FIG. 2, a drive system, illustrated as a hydraulic system is preferably utilized. Other systems, such as electric or pneumatic may be appropriate drive systems in other embodiments.

The drive system is comprised of at least one, and preferably three or more, drive cylinders 34. The drive cylinders 34 move drive pistons 36 which are coupled to the drum 18. In the preferred embodiment, a portion of the drive pistons is a threaded portion 38 to allow for the drive piston 36 to connect or couple to connection arms 40 at specific locations relative to the drive piston 36 such as with nuts 42,44. Guide rods 46 may be utilized in addition to the drive system to ensure linear movement of the drum 20 within the cavity 22 of the cylinder 12.

The drive system also includes a control unit 48 which may be operated to control movement of the plunger 20. The control unit may have a hydraulic engine which provides fluid under pressure to operate the drive cylinders 34 or may be connected to a hydraulic supply. Controls 50 allow an operator to direct the movement of the plunger 20 within the cylinder 12. Controls 50 may allow for operation of the hydraulic engine, or pump, a float switch, direction of movement selection and/or controlling valves. Gauges 52 allow for the operating parameters to be monitored. Gauges 52 may monitor air pressure, column pressure and/or drive system pressure, such as hydraulic pressure.

The control unit 48 is also preferably equipped with a controller which is a hydraulic control unit (HCU) 54. The HCU is preferably equipped with a touch screen 56 for operation of at least certain functions of the HCU 54. As discussed below, some of the operations which can be performed and or assisted by the HCU include the movement of the top flow adapter through the movement of the plunger 20 up and down a predetermined amount, movement of the plunger to a preset height, movement of the plunger in a pack process, and an auto level movement of the plunger 20 as will be discussed in further detail below. It will be understood to one of ordinary skill in the art that as the plunger 20 moves, so does the top flow adapter in the preferred embodiment.

The column 10, unlike prior art configurations, utilizes sensors which provide input to the HCU 54 which can then vary signals to control operation of certain procedures in an improved manner as will be discussed below. The cylinders 34 preferably have sensors 58 in communication therewith which can sense a pressure. Sensors 58 provide an output which is received by the HCU 56 in the preferred embodiment. Sensors 60 which sense position are also employed which provide a position relative to each of the pistons 36. Output from sensors 60 is also provided to the HCU 54.

Position sensors 60 in cooperation with the HCU 54 provide various capabilities which have not been achievable with prior art designs. First, an operator can select from one of a plurality of preset positions for the plunger 20 to be positioned relative to the cylinder 12. FIGS. 1 and 2 show two of various positions of plunger 20 relative to cylinder 12 which could be pre-selected.

In operation, the operator may utilize a touch screen 56, or other input device, to input which of the predetermined positions the plunger 20, and thus the top flow adapter, should be moved. The HCU 54 preferably then directs selective opening of valves 62 to each of the cylinders 36 to provide for the desired piston movement with the hydraulic system. Predetermined positions could be relative positions such as up or down six inches and/or to a set pre-pack position of providing the top flow adapter at two inches below the top of the column cylinder 12.

The HCU 54 also preferably normally operates in what is believed to be a new auto level configuration. Since each of the pistons 36 which control movement of the plunger 20 are equipped with position sensors 60, the output from these sensors 60 received by the HCU 54 can be utilized. The elevation of each of the pistons 36 or other elevation corresponding to each of the lifting units connected to the plunger can be monitored. Should any particular elevation deviate from one of the other measured elevations, or any two deviate from the other in the preferred embodiment a correction can be made to place the elevations back within a tolerance range of one another. Corrections can include sounding an alarm and/or stopping at least one, if not two or more of the cylinders while one or more of the others level out.

The HCU 54 can direct the selective opening and closing of at least some of the valves 62 which are in communication with respective cylinders 34 or other appropriate driver to ensure that the top flow adapter and the plunger 20 remain level within the chromatography cylinder 12. By level, it will be understand that being within a predetermined tolerance range of level will be sufficient, such as within a centimeter for a two meter diameter cylinder 12, or other appropriate first tolerance.

If the plunger 20 somehow goes beyond a second tolerance (outside of the first tolerance), it may be preferable for the HCU 54 to secure any further movement of the plunger 20 and/or sound an alarm until the situation can be addressed. The HCU 54 in the preferred embodiment provides the ability for selected cylinders 34 to be controlled to correct such a situation.

Another advantage of using the HCU 54 of the preferred embodiment is the ability to automate the packing process. The output from one or more pressure sensors 60 which could relate to back pressure on the cylinders 34 and/or pressure within the cavity 22. By having the HCU downwardly direct the plunger 20 until reaching a predetermined backpressure as measured from the sensor, and preferably while employing the auto level feature, the HCU can secure downward movement upon reaching the set pressure and/or after a predetermined time after reaching the set pressure.

The sensed pressure from one or more sensors 58 provide an input to the HCU 54 which then applies a pressure setpoint to determine a pressure error. This pressure error is applied with a damping factor to attempt to minimize overshoot of a desired pressure.

The HCU may also provide the ability to stop movement of the plunger 20, such as if the operator decided to terminate the automated packing process and/or to move the top flow adapter to a preset height.

The HCU may also provide an ability to de-pressurize the hydraulic system. This can stop top flow adapter movement and reduce top flow adapter pressure. A pneumatic pump and/or system may be vented to depressurize the hydraulic system. Other venting or depressurizing techniques could also be utilized. This provides an advantage of using a controller 48 with multiple columns 10 (i.e., once a column is set up for operation, the controller 48 can then be moved to prepare another column for operation).

The new controller 48 may now be utilized with various columns. The preferred embodiment of the controller 48 can identify the type and/or height of the column to which it is connected. This can be advantageous as different control parameters may be utilized with different sized columns. A PLC (or other computer) within the controller such as HCU, or otherwise, upon connection with a cable 64, senses inputs which can be combined as binary numbers (such as the preset open or closed condition of two switches) to identify cylinder diameter and/or cylinder stroke and/or max bed height, etc. The switches provide inputs to the HCU 54 through cable 64 or otherwise.

While the HCU 54 can provide a plurality of automated features, it is also anticipated that it can provide for manual operation including operation of separate valves 62 to respective cylinders (which was not an option in the prior art). Of course, any and potentially all of the automated features can be selected to be off through use of input such as touchscreen 56.

By using the inputs to HCU 54, alarms can be provided such as if the plunger 20, and/or top flow adapter is tilted past a predetermined tolerance, if the top flow adapter is lifted up past an upper height limit, if the column is disconnected (i.e., no top flow adapter is sensed), if the cable 64 is disconnected.

The HCU preferably includes a PLC which is provided with the controller 48. The PLC used in one operational version is an Allen-Bradley (A-B) MocroLogic 1500 Processor with I/O modules. This PLC monitors and controls the operation of three cylinders that support the plunger. The touchscreen 56 is an A-B PanelView 550. Rockwell Automation Software including RSLogix 500 were utilized to develop the PLC programming, PanelBuilder32 was utilized to develop a graphics interface and RSLink was utilized to communicate downloads to the PLC as well as interface with a PC and the touchscreen 56. Other software and hardware as known in the art could also be utilized.

The component parts, such as the drum 18, the cylinder 12, and the base are preferably constructed from stainless steel and/or high nickel alloy and/or acrylic. The drive system may be constructed out of appropriate materials including stainless steel. Three or more legs 76, only two of which are illustrated, are connected to the base 64. The drive cylinders 34 are connected to the rim 70 of the base.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method for operating a chromatography column comprising:
    providing a cylinder with a plunger connected to a drive system, said plunger moveable within a cavity of the cylinder in an operational mode, said drive system having at least two drivers operably coupled to the plunger,
    position sensors respectively associated with the at least two drivers,
    a controller in communication with the position sensors, wherein said controller evaluates data relative to positions of the at least two drivers; providing at least one output for use in controlling operation of the at least two drivers with the controller to position the plunger up or down at least one of a predetermined distance and to at least one preset elevation relative to the cylinder while maintaining the plunger level.

2. The method of claim 1 wherein the controller calculates an error using the data derived from the position sensors, and if an error exceeds a predetermined amount, providing an output to for at least one of temporarily stopping at least one of the drivers, at least temporarily stopping all of the drivers and sounding an alarm.

3. The method of claim 2 wherein said error is calculated during at least one of up and down movement of the plunger within the cavity.

4. The method of claim 3 wherein when said error exceeds the predetermined amount, said controller provides a signal to stop operation of at least one of the drivers while providing a signal to continue operation of at least of the other drivers to reduce the error.

5. The method of claim 4 wherein the predetermined amount is a first predetermined amount, and if a second predetermined amount is exceeded said controller provides a signal to stop operation of all drivers, wherein said second predetermined amount is greater than the first predetermined amount.

6. The method of claim 1 wherein the predetermined amount is at least about six inches.

7. The method of claim 1 wherein the controller is operably coupled to an input device and said input device provides for an ability to select at least one movement of the plunger by the controller while receiving input from the position sensors.

8. The method of claim 7 wherein the input device is a touchscreen.

9. The method of claim 7 wherein the movement is a movement to one of a plurality of pre-set positions.

10. The method of claim 9 wherein a damping factor is utilized by the controller with input from at least one of the sensors to locate the plunger at at least about the specific elevation.

11. The method of claim 1 wherein the controller receives an input from a source related to the cylinder identifying at least one of a type and a height of the cylinder.

12. The method of claim 1 further comprising at least one pressure sensor coupled to at least one of the at least one driver sensing a pressure related to a resistance pressure exerted on the plunger by media within the cavity.

13. The method of claim 12 wherein the pressure sensor provides an input to the controller and when the controller is placed in a pack configuration with the plunger directed by the controller until at least about a predetermined pressure value is obtained, and after obtaining the at least about a predetermined pressure value, said controller stopping movement of the plunger.

14. The method of claim 12 wherein the controller calculates an error using the data derived from the position sensors, and if an error exceeds a predetermined amount, providing an output to for at least temporarily stopping at least one of the drivers, at least temporarily stopping all of the drivers and sounding an alarm.

15. A method of operating a chromatography column comprising:
providing a cylinder with a plunger connected to a drive system, said plunger moveable within a cavity of the cylinder in an operational mode, said drive system having at least two drivers operably coupled to the plunger,
at least two pressure sensors coupled respectively to the at least two drivers sensing pressures related to a resistance pressure exerted on the plunger by media within the cavity, and
a controller in communication with the at least two pressure sensors, and evaluating data with the controller relative to the pressures provided by the at least two pressure sensors, and said controller providing at least one output for use in controlling operation of the at least two drivers while maintaining the plunger level.

16. The method of claim 15 wherein the pressure sensor provides an input to the controller and when the controller is placed in a pack configuration with the plunger directed by the controller until at least about a predetermined pressure value is obtained, and after obtaining the at least about a predetermined pressure value, said controller stopping movement of the plunger.

17. The method of claim 15 further comprising at least one position sensor sensing a position relative to at least one of the plunger and at least one of the at least two drivers, said position sensor in communication with the controller, and said controller having at least one operational mode in which input from the position sensor is utilized by the controller to provide movement through the at least one driver.

18. The method of claim 17 wherein the controller has at least one operational mode in which selection of a desired movement by an operator results in the desired movement under the control of the controller in communication with the position sensor of one of a predetermined distance and to a predetermined elevation.

19. The method of claim 15 further comprising at least two drivers connected to the plunger with each driver having a position sensor providing positions relative thereto, and wherein the controller calculates an error using the data derived from the position sensors, and if an error exceeds a predetermined amount, providing an output to for at least one of temporarily stopping at least one of the drivers, at least temporarily stopping all of the drivers and sounding an alarm.

20. The method of claim 19 wherein the pressure sensor provides an input to the controller and when the controller is placed in a pack configuration with the plunger directed by the controller until at least about a predetermined pressure value is obtained, and after obtaining the at least about a predetermined pressure value, said controller stopping movement of the plunger.

* * * * *